United States Patent
Lindemann et al.

(10) Patent No.: US 8,672,984 B2
(45) Date of Patent: Mar. 18, 2014

(54) METHOD AND APPARATUS FOR RETAINING SCREW IN A PLATE

(75) Inventors: Gary S. Lindemann, Collierville, TN (US); Larry Gause, Memphis, TN (US); Robert A. Farris, Cordova, TN (US); Regis W. Haid, Jr., Atlanta, GA (US); Stephen Papadopoulos, Paradise, AZ (US); Rick Sasso, Indianapolis, IN (US); Volker Sonntag, Phoenix, AZ (US); Vincent C. Traynelis, Iowa City, IA (US); Iain Kalfas, Beachwood, OH (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 748 days.

(21) Appl. No.: 12/777,934

(22) Filed: May 11, 2010

(65) Prior Publication Data

US 2010/0222780 A1 Sep. 2, 2010

Related U.S. Application Data

(63) Continuation of application No. 10/870,026, filed on Jun. 17, 2004, now Pat. No. 7,727,266.

(51) Int. Cl.
*A61B 17/80* (2006.01)
(52) U.S. Cl.
USPC ............................................. 606/289
(58) Field of Classification Search
USPC ........... 606/246, 279–281, 286, 289–291, 70, 606/71; 403/7, 9, 330, 350, 374.1, 379.2, 403/409.1
See application file for complete search history.

(56) References Cited

U.S. PATENT DOCUMENTS

| | | |
|---|---|---|
| 5,085,548 A | 2/1992 | Moyles |
| 5,098,435 A | 3/1992 | Stednitz et al. |
| 5,261,910 A | 11/1993 | Warden et al. |
| 5,290,312 A | 3/1994 | Kojimoto et al. |
| 5,318,567 A | 6/1994 | Vichard |
| 5,364,399 A | 11/1994 | Lowery et al. |
| 5,470,333 A | 11/1995 | Ray |
| 5,484,439 A | 1/1996 | Olson et al. |
| 5,484,440 A | 1/1996 | Allard |
| 5,520,690 A | 5/1996 | Errico et al. |
| 5,531,746 A | 7/1996 | Errico et al. |
| 5,549,607 A | 8/1996 | Olson et al. |
| 5,549,612 A | 8/1996 | Yapp et al. |
| 5,562,661 A | 10/1996 | Yoshimi et al. |
| 5,578,034 A | 11/1996 | Estes |
| 5,607,426 A | 3/1997 | Ralph et al. |
| 5,611,800 A | 3/1997 | Davis et al. |
| 5,616,144 A | 4/1997 | Yapp et al. |

(Continued)

FOREIGN PATENT DOCUMENTS

| | | |
|---|---|---|
| EP | 1 346 697 A2 | 9/2003 |
| EP | 1346697 A2 | 9/2003 |
| FR | 2 794 963 A1 | 12/2000 |
| WO | WO 95/35067 | 12/1995 |

*Primary Examiner* — Pedro Philogene
*Assistant Examiner* — David Comstock

(57) ABSTRACT

A retention system for maintaining a screw to a vertebral plate is described herein. One or more screws extend through apertures within the vertebral plate. A cavity is positioned adjacent to and overlaps into the aperture. A ring is positioned within the cavity and held in position by a cap. The cap attaches to the plate to prevent removal of the ring. The ring is deflectable between a first shape to allow the screw to be inserted and removed from the aperture, and a second shape to prevent screw back-out from the aperture.

20 Claims, 5 Drawing Sheets

(56) References Cited

U.S. PATENT DOCUMENTS

| | | |
|---|---|---|
| 5,634,925 A | 6/1997 | Urbanski |
| 5,676,666 A | 10/1997 | Oxland et al. |
| 5,681,311 A | 10/1997 | Foley et al. |
| 5,713,900 A | 2/1998 | Benzel et al. |
| 5,728,098 A | 3/1998 | Sherman et al. |
| 5,735,853 A | 4/1998 | Olerud |
| 5,735,899 A | 4/1998 | Schwartz et al. |
| 5,766,254 A | 6/1998 | Gelbard |
| 5,800,433 A | 9/1998 | Benzel et al. |
| 5,843,082 A | 12/1998 | Yuan et al. |
| 5,876,402 A | 3/1999 | Errico et al. |
| 5,904,683 A | 5/1999 | Pohndorf et al. |
| 5,931,838 A | 8/1999 | Vito |
| 5,954,722 A | 9/1999 | Bono |
| 5,954,725 A | 9/1999 | Sherman et al. |
| 6,004,321 A | 12/1999 | Graser |
| 6,017,345 A | 1/2000 | Richelsoph |
| 6,030,389 A | 2/2000 | Wagner et al. |
| 6,036,693 A | 3/2000 | Yuan et al. |
| 6,077,267 A | 6/2000 | Huene |
| 6,117,135 A | 9/2000 | Schlafer |
| 6,117,713 A | 9/2000 | Hoshino et al. |
| 6,132,434 A | 10/2000 | Sherman et al. |
| 6,152,927 A | 11/2000 | Farris et al. |
| 6,159,213 A | 12/2000 | Rogozinski |
| 6,189,422 B1 | 2/2001 | Stihl |
| 6,193,720 B1 | 2/2001 | Yuan et al. |
| 6,224,602 B1 | 5/2001 | Hayes |
| 6,228,085 B1 | 5/2001 | Theken et al. |
| 6,235,034 B1 | 5/2001 | Bray |
| 6,241,731 B1 | 6/2001 | Fiz |
| 6,258,089 B1 | 7/2001 | Campbell et al. |
| 6,261,291 B1 | 7/2001 | Talaber et al. |
| 6,273,888 B1 | 8/2001 | Justis |
| 6,273,889 B1 | 8/2001 | Richelsoph |
| 6,287,311 B1 | 9/2001 | Sherman et al. |
| 6,302,883 B1 | 10/2001 | Bono |
| 6,306,136 B1 | 10/2001 | Baccelli |
| 6,331,179 B1 | 12/2001 | Fried et al. |
| 6,342,055 B1 | 1/2002 | Eisemann et al. |
| 6,361,537 B1 | 3/2002 | Anderson |
| 6,383,186 B1 | 5/2002 | Michelson |
| 6,398,783 B1 | 6/2002 | Michelson |
| 6,402,756 B1 | 6/2002 | Ralph et al. |
| 6,413,259 B1 | 7/2002 | Lyons |
| 6,416,528 B1 | 7/2002 | Michelson |
| 6,428,542 B1 | 8/2002 | Michelson |
| 6,440,136 B1 | 8/2002 | Gambale et al. |
| 6,454,769 B2 | 9/2002 | Wagner et al. |
| 6,454,771 B1 | 9/2002 | Michelson |
| 6,454,773 B1 | 9/2002 | Sherman et al. |
| 6,485,491 B1 | 11/2002 | Farris et al. |
| 6,503,250 B2 | 1/2003 | Paul |
| 6,513,814 B2 | 2/2003 | White |
| 6,527,776 B1 | 3/2003 | Michelson |
| 6,533,786 B1 | 3/2003 | Needham et al. |
| 6,592,586 B1 | 7/2003 | Michelson |
| 6,599,290 B2 | 7/2003 | Bailey et al. |
| 6,602,255 B1 | 8/2003 | Campbell et al. |
| 6,602,256 B1 | 8/2003 | Hayes |
| 6,602,257 B1 | 8/2003 | Thramann |
| 6,605,090 B1 | 8/2003 | Trieu et al. |
| 6,620,163 B1 | 9/2003 | Michelson |
| 6,626,907 B2 | 9/2003 | Campbell et al. |
| 6,652,525 B1 | 11/2003 | Assaker et al. |
| 6,656,181 B2 | 12/2003 | Dixon et al. |
| 6,660,004 B2 | 12/2003 | Barker et al. |
| 6,666,867 B2 | 12/2003 | Ralph et al. |
| 6,669,700 B1 | 12/2003 | Farris et al. |
| 6,679,883 B2 | 1/2004 | Hawkes et al. |
| 6,682,564 B1 | 1/2004 | Duarte |
| 6,689,134 B2 | 2/2004 | Ralph et al. |
| 6,695,845 B2 | 2/2004 | Dixon et al. |
| 6,695,846 B2 | 2/2004 | Richelsoph et al. |
| 6,702,817 B2 | 3/2004 | Beger et al. |
| 6,755,833 B1 | 6/2004 | Paul et al. |
| 6,761,719 B2 | 7/2004 | Justis et al. |
| 6,780,186 B2 | 8/2004 | Errico et al. |
| 6,793,658 B2 | 9/2004 | LeHuec et al. |
| 2002/0013586 A1 | 1/2002 | Justis et al. |
| 2002/0045897 A1 | 4/2002 | Dixon et al. |
| 2002/0045898 A1 | 4/2002 | Freid et al. |
| 2002/0058939 A1 | 5/2002 | Wagner et al. |
| 2002/0065517 A1 | 5/2002 | Paul |
| 2002/0082603 A1 | 6/2002 | Dixon et al. |
| 2002/0111630 A1 | 8/2002 | Ralph et al. |
| 2002/0120273 A1 | 8/2002 | Needham et al. |
| 2002/0128655 A1 | 9/2002 | Michelson |
| 2002/0147450 A1 | 10/2002 | LeHuec et al. |
| 2002/0183754 A1 | 12/2002 | Michelson |
| 2002/0183755 A1 | 12/2002 | Michelson |
| 2003/0018335 A1 | 1/2003 | Michelson |
| 2003/0023242 A1 | 1/2003 | Harrington, Jr. |
| 2003/0036759 A1 | 2/2003 | Musso |
| 2003/0040749 A1 | 2/2003 | Grabowski et al. |
| 2003/0045880 A1 | 3/2003 | Michelson |
| 2003/0060828 A1 | 3/2003 | Michelson |
| 2003/0093082 A1 | 5/2003 | Campbell et al. |
| 2003/0105462 A1 | 6/2003 | Haider |
| 2003/0149434 A1 | 8/2003 | Paul |
| 2003/0181912 A1 | 9/2003 | Michelson |
| 2003/0187440 A1 | 10/2003 | Richelsoph et al. |
| 2003/0191471 A1 | 10/2003 | Michelson |
| 2003/0191472 A1 | 10/2003 | Michelson |
| 2003/0208204 A1 | 11/2003 | Bailey et al. |
| 2003/0225409 A1 | 12/2003 | Freid et al. |
| 2003/0236528 A1 | 12/2003 | Thramann |
| 2004/0019353 A1 | 1/2004 | Freid et al. |
| 2004/0030336 A1 | 2/2004 | Khanna |
| 2004/0030338 A1 | 2/2004 | Paul |
| 2004/0034352 A1 | 2/2004 | Needham et al. |
| 2004/0034354 A1 | 2/2004 | Paul |
| 2004/0039387 A1 | 2/2004 | Gause et al. |
| 2004/0068319 A1 | 4/2004 | Cordaro |
| 2004/0087951 A1 | 5/2004 | Khalili |
| 2004/0097934 A1 | 5/2004 | Farris et al. |
| 2004/0097935 A1 | 5/2004 | Richelsoph et al. |
| 2004/0097938 A1 | 5/2004 | Alleyne |
| 2004/0097940 A1 | 5/2004 | Paul |
| 2004/0106924 A1 | 6/2004 | Ralph et al. |
| 2004/0127897 A1 | 7/2004 | Freid et al. |
| 2004/0127899 A1 | 7/2004 | Konieczynski et al. |
| 2004/0127900 A1 | 7/2004 | Konieczynski et al. |
| 2004/0127904 A1 | 7/2004 | Konieczynski et al. |
| 2004/0133205 A1 | 7/2004 | Thramann et al. |
| 2004/0153069 A1 | 8/2004 | Paul |
| 2004/0158246 A1 | 8/2004 | Assaker et al. |
| 2004/0181227 A1 | 9/2004 | Khalili |
| 2004/0210219 A1 | 10/2004 | Bray |
| 2004/0220566 A1 | 11/2004 | Bray |
| 2004/0220571 A1 | 11/2004 | Assaker et al. |
| 2004/0236333 A1 | 11/2004 | Lin |

METHOD AND APPARATUS FOR RETAINING SCREW IN A PLATE

This application is a continuation of U.S. patent application Ser. No. 10/870,026, filed Jun. 17, 2004, the disclosure of which is incorporated herein by reference.

BACKGROUND

The human spine is a biomechanical structure consisting of thirty-three vertebral members and is responsible for protecting the spinal cord, nerve roots and internal organs of the thorax and abdomen. The spine also provides structural support for the body while permitting flexibility of motion. In certain surgical procedures it is necessary to secure together two or more of the vertebral members. The procedure may be necessary for example as a result of physical trauma or degenerative diseases.

One type of surgical procedure includes attachment of a vertebral plate to the vertebral members. The vertebral plate is sized to extend across two or more of the vertebral members. One or more bone screws extend through apertures in the plate and into the vertebral members to secure the plate. One issue with the attachment is the screws may tend to loosen and back-out of the vertebral members. Screw retention devices may be necessary to prevent the screw from backing-out of the vertebral members.

One type of screw retention device utilizes a snap ring that expands as the screw is inserted into the aperture and then retracts to a smaller diameter once the screw head has passed the level of the snap ring. One issue with previous snap ring designs is the inability to use the rings with a variety of different screws. These designs may not be effective for both variable angle and fixed angle screws, or may require specialty screws that are designed for only a limited application. Additionally, these previous designs have needed a larger plate thickness to accommodate the snap ring. Another issue is the difficulty for the surgeon to visually see when the lock ring has moved over the top of the screw once the screw has passed the level of the snap ring. Some designs also prevent or limit the ability of the surgeon to tactilely feel the movement of the snap ring as it moves over the top of the screw. Additionally, some designs interfere with the surgeon's feel of the screw purchasing within the bone.

SUMMARY

The present invention is directed to a system and method of retaining screws within a vertebral plate and preventing screw back-out. The invention includes a variety of embodiments, with one embodiment having a plate with at least one aperture for receiving a screw. A cavity is positioned within the plate and partially overlaps into the aperture. A ring is positioned within the cavity and held in position by a cap. The ring is resilient and changes shape between an original shape that extends partially over the aperture, and a deflected shape away from the aperture.

Methods of retaining the screw are also disclosed. One method includes positioning a resilient member within a cavity in the plate such that it partially extends over the aperture. The next step comprises placing a cap over the cavity and attaching the cap to the plate to prevent the resilient member from being removed from the plate. The next step includes inserting a screw into the aperture and deflecting the resilient member away from the aperture. The screw is inserted into the vertebral member a predetermined distance, and the resilient member is returned to its original shape over the aperture and over the screw to prevent the screw from backing-out of the aperture.

DETAILED DESCRIPTION

Figure 1:
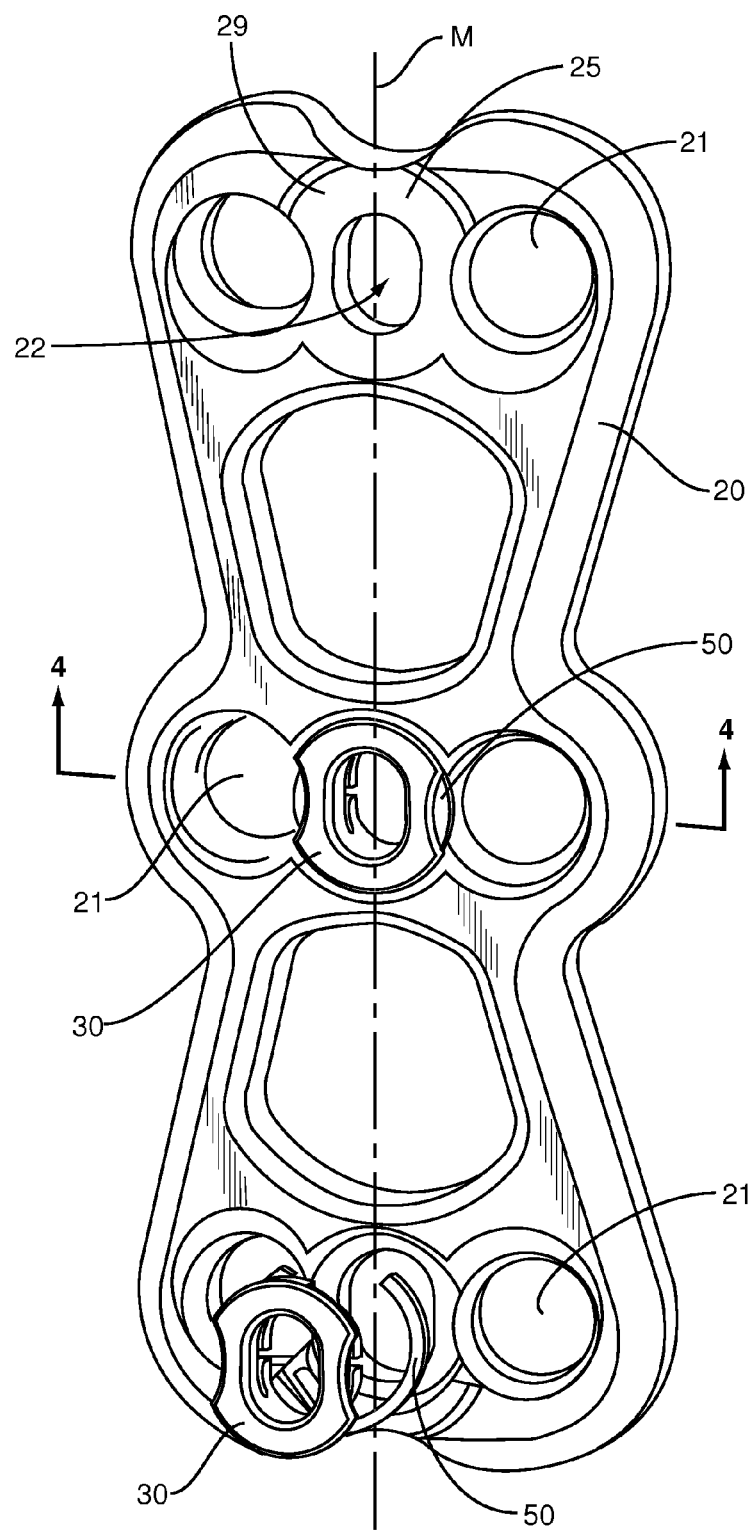
FIG. 1 is a partially-exploded front view of the plate with a ring and cap according to one embodiment of the present invention.

The present invention is directed to a retention system for maintaining the position of a screw 70 relative to a vertebral plate 20. FIG. 1 illustrates one embodiment of a vertebral plate 20 having one or more apertures 21. A cavity 22 is positioned adjacent to and overlaps into the aperture 21. A ring 50 is positioned within the cavity 22 and held in position by a cap 30. The cap 30 attaches to the plate 20 to prevent removal of the ring 50. The ring 50 is resilient and changes shape between an original shape that extends over an aperture 21 to prevent screw back-out, and a deflected shape that allows insertion and removal of the screw from the aperture 21 (see FIGS. 4 and 5).

The plate 20 is sized to extend across one or more vertebral members 100. Apertures 21 extend through the plate 20 between a top surface 23 and a bottom surface 24 to receive the bone screws 70. The apertures 21 may have a variety of sizes and orientations depending upon the specific application. The cavity 22 is positioned adjacent to the aperture 21 and includes a counterbore 29 that extends inward into the plate 20 from the top surface 23. The cavity 22 may extend entirely through the plate 20, or may extend only a limited distance into the plate 20 from the top surface 23. A depth that the counterbore 29 extends into the top surface 23 may likewise vary depending upon the application. The counterbore 29 may form an upper ledge 25 to accommodate the ring 50 as will be explained later. In one embodiment, the cavity 22 and counterbore 29 are co-axially aligned and each has a substantially circular shape. Various other shapes may also be employed and are contemplated by the present invention. In one embodiment, the cavity 22 and counterbore 29 are both centered within the medial plane M of the plate 20. The plate 20 may have both a medial and lordotic curve to conform to the dimensions of the vertebral members 100. The cavity 22 may further include elements to assist with retaining the cap 30. For example, a second counterbore 28 may be formed in the bottom surface 24 of the plate 20.

Figure 2:
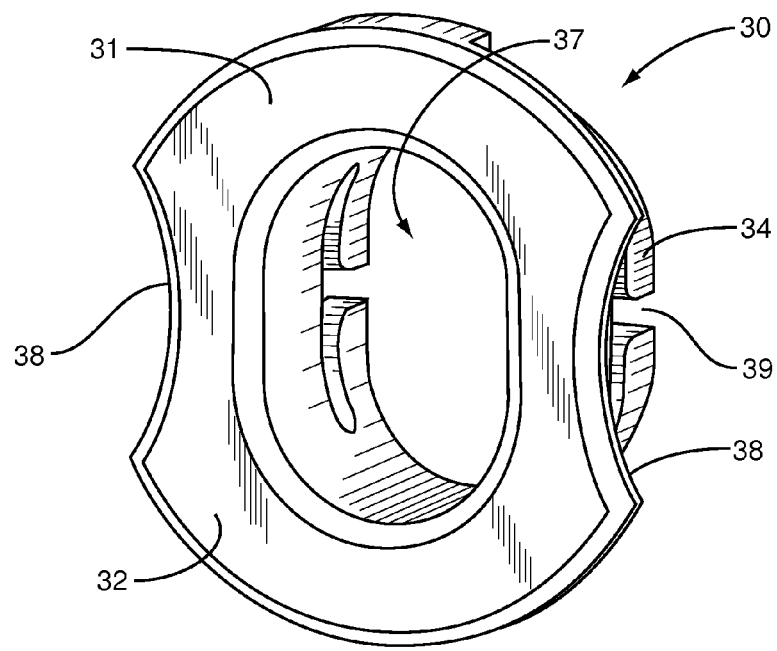
FIG. 2 is a front perspective view of the cap according to one embodiment of the present invention.
Figure 3:
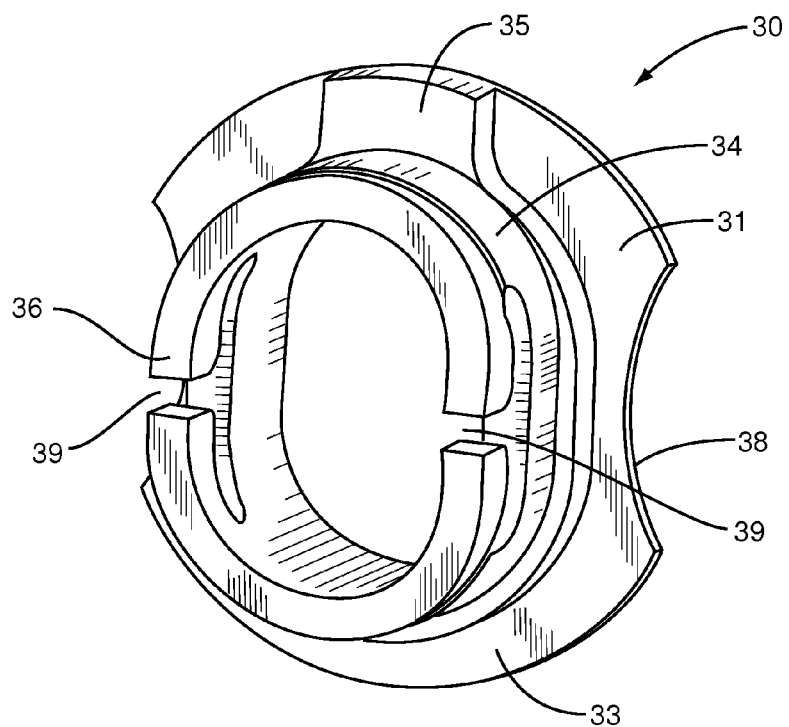
FIG. 3 is a back perspective view of the cap according to one embodiment of the present invention.

FIGS. 2 and 3 illustrate front and rear perspective views of the cap 30 removed from the plate 20. The cap 30 includes a flange 31 and an outwardly extending plug 34. The flange 31 includes an upper surface 32 and a lower surface 33. When mounted in the plate 20, the flange 31 seats within the counterbore 29 with the upper surface 32 substantially flush with the top surface 23 of the plate 20. The plug 34 has a width generally corresponding to the size of the cavity 22. Ears 36 and slots 39 may be positioned at the edge of the plug 34 opposite the flange 31 and mate with the lower counterbore 28.

A window 37 may be formed in the plug 34 and provide a contact point for grasping and manipulating the cap 30 and/or plate 20 during a surgical procedure. The window 37 may also be used for location and orientation of surgical instruments, such as plate holders, drills, taps, and screw guides. The window 37 may extend through the entire cap 30, or may extend only a limited distance inward from the upper surface 32 of the flange 31. The window 37 may have a shape to allow medial alignment of the plate 20, such as the oval shape illustrated in the Figures.

Figure 4:
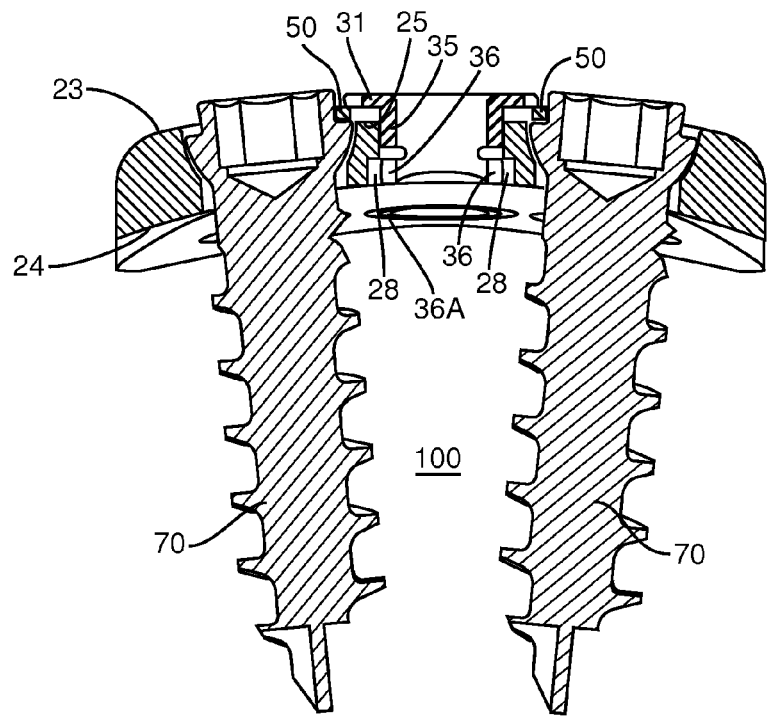
FIG. 4 is a cross-sectional view illustrating the ring extending over a pair of screws according to one embodiment of the present invention.
Figure 5:
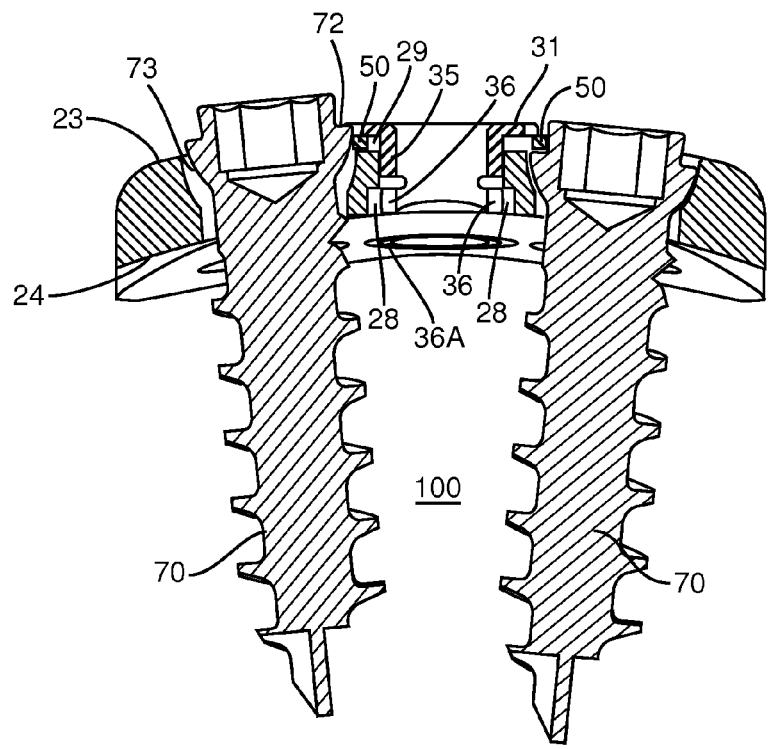
FIG. 5 is a cross-sectional view illustrating the ring extending over a first aperture and being biased inward away from a second aperture according to one embodiment of the present invention.

The cap 30 is attached to the plate 20 and maintains the ring 50 within the cavity 22. A variety of means may be used for attaching the cap 30 to the plate 20, including for example, interference fit, snap fit, staking, and swaging. In one embodiment, the cap 30 has external threads along the plug 34 that mate with threads on the inner wall of the cavity 22. The cap 30 may also be attached via a removable or non-removable fastener, such as screw, rivet, and the like. FIGS. 4 and 5 illustrate one method of attaching the cap 30 to the plate 20. The external features of the plug 34 are sized to contact the sidewall of the cavity 22 and provide an interference fit. Additionally, the ears 36 extend outward into the lower counterbore 28 to further secure the cap 30. The ears 36 may be deformed into the lower counterbore 28 during the manufacturing process or alternatively by the surgeon or other medical personnel prior to or during the surgery. In one specific embodiment, the ears 36 are grasped by a tool and bent outward away from the cavity thus enlarging the width and preventing the cap 30 from being removed from the plate 20. In another embodiment, the cap 30 is constructed of a resilient material. When inserted into the cavity 22, the ears 36 resiliently rebound outward into the counterbore 28. The position of the ears 36 within the counterbore 28 is illustrated in FIGS. 4 and 5. Ears 36A illustrate the mounting of the adjacent upper cap 30 (i.e., the cap 30 positioned adjacent to the cross-sectionally cut middle cap 30). In these embodiments, the cap 30 may be retained by only the interference fit, only the deformed ears 36, or by both.

Figure 6:
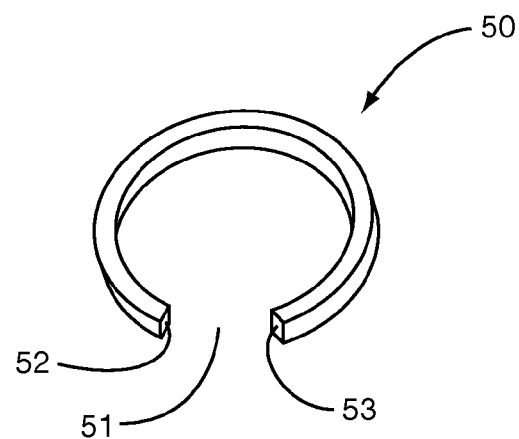
FIG. 6 is a perspective view of the ring according to one embodiment of the present invention.

The ring 50 is positioned within the cavity 22 to prevent back-out of the screw 70. The ring 50 is constructed of a resilient spring material that is elastic and deflectable between an original shape when mounted in the cavity 22 that extends outward into the aperture 21, and a deflected state away from the aperture 21 to allow removal and insertion of the screw 70 relative to the aperture 21. FIG. 6 illustrates one embodiment of the ring 50 having a substantially circular shape with inner and outer diameters and a compression slot 51 formed between first and second ends 52, 53. Ring 50 has upper and lower surfaces with the lower surface positioned towards the upper ledge 25 of the counterbore 29. In one embodiment, the lower surface is substantially flat to contact the screw 70 when the ring 50 extends into the aperture 21. FIG. 6 illustrates one embodiment of ring 50 having a rectangular cross-sectional shape. Another embodiment features a triangular cross-sectional shape.

The ring 50 may be constructed of a material having elastic properties. In one embodiment, the ring 50 is made of a Nickel-Titanium alloy that is heat treated to achieve superelastic properties when exposed to a temperature range within the human body. The ring 50 may also be constructed of other materials, for example, peek, titanium, or stainless steel. The term "ring" is used broadly herein to refer to the member positioned within the cavity. It is understood that the member may have a variety of different shapes and sizes.

In one embodiment, the diameter of the counterbore 29 is less than an outer diameter of the ring 50. This causes the ring 50 to be pre-loaded in the original shape when seated in the counterbore 29. The pre-loaded condition causes the compression slot 51 to be reduced and gives the ring 50 additional expansion force to extend outward over the aperture 21. The amount of deflection of the ring 30 may vary depending upon the application. Deflection may occur on one side of the ring 30, or on both sides such as would occur in an embodiment as illustrated in FIGS. 1, 4, and 5 as both screws 70 were being inserted.

Figure 7:
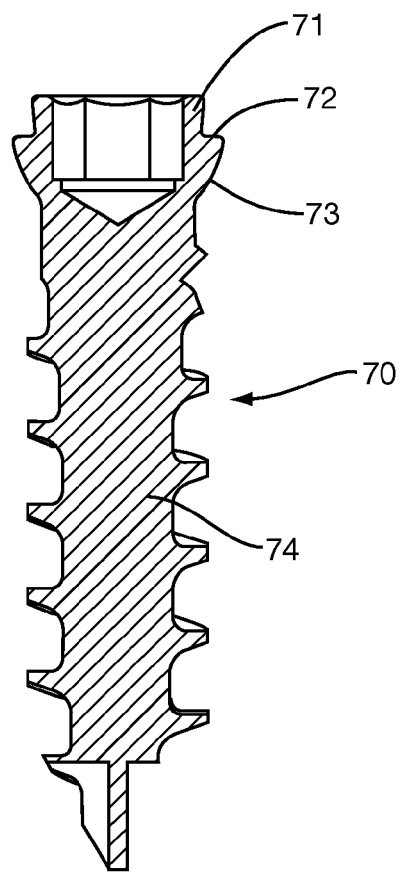
FIG. 7 is a cross-sectional view of a screw mounted within the plate according to one embodiment of the present invention.
Figure 8:
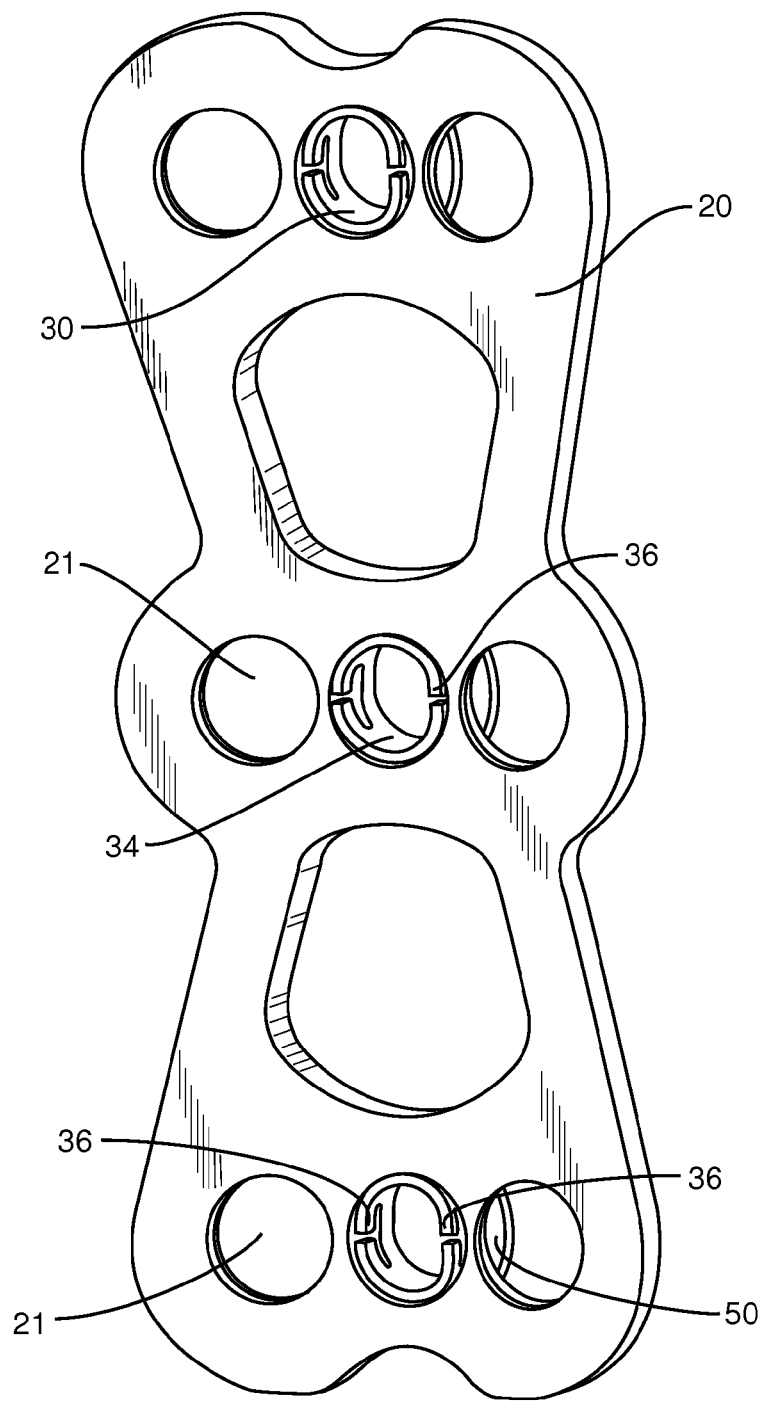
FIG. 8 is a rear perspective view of the plate with caps mounted within the cavities adjacent to the screw-receiving apertures according to one embodiment of the present invention.

FIG. 7 illustrates one embodiment of the screw 70 and includes a head 71, shelf 72, spherical radius 73 and shaft 74. The shelf 72 extends outward beyond the head 71 and provides a platform for receiving the ring 50. The shelf 72 may be substantially flat to provide a good contacting surface for the flat surface of the ring 50. The spherical radius 73 has a maximum width at the shelf 72 and reduces to a minimum width at the shaft 74.

FIGS. 1, 4, and 5 illustrate one embodiment of the invention having a cavity 22 positioned between and overlapping into two apertures 21. Each of the apertures 21 and cavities 22 has a substantially circular shape with the cavity 22 having a counterbore 29 that overlaps into the apertures 21. The ring 50 has an original shape that extends outward and overlaps into the apertures 21, and a deflected shape in a non-overlapping position away from the aperture 21. In one embodiment, the ring 50 is in the original shape prior to screw insertion, and after the screw 70 has been inserted into the aperture 21 and the shelf 72 passes below the level of the ring 50. FIG. 4 illustrates the ring 50 in the original shape where the shelf 72 is below the level of the ring 50. The resilient nature of the ring 50 causes it to return toward the original shape and extend over the shelf 72. The ring 50 position prior to screw insertion is illustrated within the middle cavity 22 and apertures 21 of the plate 20 in FIG. 1.

The insertion and removal of the screw 70 from the aperture 21 causes the ring 50 to deflect and move away from the aperture 21. One example is illustrated within the left screw 70 illustrated in FIG. 5. The force of the insertion or removal deflects the ring 50 inward from the aperture 21 and further into the counterbore 29.

The ring 50 overlaps into the apertures 21 a distance once the screw 70 has been inserted to prevent back-out of the screw 70. In one embodiment, the ring 50 extends outward beyond the edge of the cap flange 31 to allow visual confirmation of the position by a surgeon. This may further be assisted by coloring the ring 50 and screw 70 with contrasting colors to make it easier to visually observe the relative position of these elements.

The cap flange 31 may have a shape that conforms to the adjacent aperture 21 and prevents the flange 31 from extending over the aperture 21 when the cap 30 is mounted to the plate 20. As illustrated in FIGS. 2 and 3, the flange 31 has curved edges 38 that conform to the outer circumference of the aperture 21. Therefore, the flange 31 does not overlap into the aperture 21 while still allowing the ring 50 to overlap into the aperture 21.

The ring 50 is positioned in the space created between the cap 30 and cavity 21. In one embodiment, both the cap 30 and ring 50 are co-axially aligned within the cavity 22. As illustrated in FIGS. 2 and 3, a tab 35 extends outward from the cap 30 to fit within the ring slot 51 and prevent rotation of the ring 50. The tab 35 includes first and second edges that are distanced apart to fit within the slot 51 of the ring 50. This prevents rotation of the ring 50 to a position where the slot 51 is over the aperture 21 and potentially allows the screw 70 to back-out. Tab 35 seats against the upper ledge 25 of the counterbore 29 when the cap 30 is in the cavity 22.

As the screw 70 is inserted into the aperture 21, the spherical radius 73 contacts the ring 50 and deflects it away from the aperture 21. As the insertion of the screw 70 continues, the ring 50 is further deflected from its original shape and away from the aperture 21. After insertion has progressed beyond the point where the spherical radius 73 is below ring 50, the ring 50 returns towards the original shape to extend over the shelf 72. The snapping action of the ring 50 extending over the shelf 72 may be tactilely detected by the surgeon and provide assurance that the ring 50 is seated over the screw 70 to prevent back-out. The elastic property of the ring 50 causes a snapping action as the screw passes and does not require the surgeon to proactively engage the ring 50.

Another embodiment of the device includes the ring 50 attached to the cap 30. The ring 50 and cap 30 combination may be a single integral piece, or the ring 50 may be a separate piece that is fixedly attached to the cap 30. In these embodiments, the combination positions the ring 50 over the apertures 21 in the original shape and allows the ring 50 to be deflected upon screw 70 insertion and removal.

The original shape of the ring 50 is positioned to extend over one or more apertures 21. This original shape may not be the neutral position of the ring 50. By way of example, the shape of the ring 50 may be constrained by the counterbore 29 and have a smaller outer width than if the ring 50 were more freely positioned within a larger space. Additionally, the ring 50 may be in a more deflected state when it returns over the aperture 21 after insertion of the screw 70. In one instance, screw 70 is in the original shape and extends over the aperture 21 a first amount. During screw 70 insertion, ring 50 deflects away from the aperture 21 to a second shape. After screw 70 insertion, ring 50 snaps back over the screw 70 to a third shape. This third shape may be the same as the original shape, or may be different depending on the position and size of the screw. By way of example, the ring 50 may contact the screw head 71 in the third shape and prevent the ring 50 from fully returning to its original shape.

The ring 50 may further deflect along a single side, or along more than one side. In the embodiment illustrated in FIGS. 1, 4, and 5, ring 50 extends into two apertures 21 and therefore can be deflected along two separate sides as screws 70 are inserted into the respective apertures 21. In another embodiment where the ring 50 extends only into a single aperture 21, the ring 50 will deflect along a single side.

The term vertebral member is used generally to describe the vertebral geometry comprising the vertebral body, pedicles, lamina, and processes. The device may be sized and shaped, and have adequate strength requirements to be used within the different regions of the vertebra including the cervical, thoracic, and lumbar regions.

FIG. 1 is included in part to illustrate the relative positioning of the plate 20, ring 50, and cap 30. Neither cap 30 nor ring 50 is attached to the upper cavity 22 to illustrate the position of the cavity 22 and counterbore 29 relative to the adjacent apertures 21. A cap 30 and ring 50 are mounted in the middle cavity to illustrate the ring 50 extending outward into the adjacent apertures 21 when there are no screws 70. The lower cavity 22 illustrates the cap 30 and ring 50 in an exploded view.

The present invention may be carried out in other specific ways than those herein set forth without departing from the scope and essential characteristics of the invention. The ring 50 may also have a circular, oval, or elongated cross-sectional shape. In one embodiment, the ears 36 are positioned within the lower counterbore 28 and are either flush or recessed within the bottom surface 24 of the plate so as not to interfere with positioning on the vertebral member 100. In one embodiment, the ring 50 extends over the screw head 71 to prevent screw back-out. In this embodiment, the screw 70 may or may not include a shelf 72 and spherical radius 73. In one embodiment, the plug 34 and flange 31 form an angle of about 90°. The retaining system has been discussed in the context of a vertebral plate; however, the system is also applicable to other applications in the body using plates and attachment screws. In one embodiment where the cavity 22 is positioned between two apertures 21, a center of the cavity 22 is positioned along a line formed between the centers of the two apertures 21. The present embodiments are, therefore, to be considered in all respects as illustrative and not restrictive, and all changes coming within the meaning and equivalency range of the appended claims are intended to be embraced therein.

What is claimed is:

1. A screw retaining system comprising:
   a plate with a cavity positioned between first and second apertures;
   an elastic member at the cavity and being deformable between a first shape and a second shape; and
   a cap attached to the plate and extending over the cavity and the elastic member, the cap having a shape such that the cap does not overlap with the first and second apertures; the elastic member extending outward from opposing sections of the cap and into the apertures in the first shape and positioned away from the apertures in the second shape.

2. The system of claim 1, wherein the cap is positioned between the apertures and has an hourglass shape with a first curved edge that aligns with the first aperture and a second curved shape that aligns with the second aperture.

3. The system of claim 1, wherein a center of the cavity is positioned along a straight line formed between centers of the first and second apertures.

4. The system of claim 1, wherein an upper surface of the cap is flush with a top surface of the plate when the elastic member is mounted to the plate.

5. The system of claim 1, wherein the cap is positioned within a slot in the elastic member to limit rotation of the elastic member within the cavity.

6. The system of claim 1, wherein an edge of the cap has a curved section that aligns with the first aperture such that the cap does not overlap with the first aperture.

7. A screw retaining system comprising:
   a plate with a first surface and a second surface;
   an aperture that extends through the plate;
   a counterbore that extends a limited distance into the first surface, the counterbore abutting with the aperture; an elastic member positioned within the counterbore and being deformable between a first shape that extends into the aperture and a second shape positioned away from the aperture;

a cap attached to the plate and extending over the elastic member and the counterbore to attach the elastic member to the plate, the cap including a scalloped section that aligns with an edge of the aperture such that the cap does not overlap with the aperture; a section of the elastic member extends outward beyond the scalloped section and into the aperture in the first shape, and the section being at least partially positioned under the cap in the second shape.

8. The system of claim 7, wherein the elastic member has a C-shape with first and second spaced apart ends that form a slot.

9. The system of claim 8, wherein the cap is positioned in the slot to limit rotation of the elastic member within the counterbore.

10. The system of claim 7, further comprising a second aperture that extends through the plate at the counterbore and the cap includes an outwardly-extending plug that fits within the second aperture.

11. The system of claim 10, wherein the plug includes a pair of opposing arms separated by a gap that extends longitudinally along the arms for the plug to be flexible.

12. The system of claim 7, wherein the elastic member includes an upper surface and a lower surface, the upper surface being in contact with an underside of the cap and the lower surface being in contact with a bottom surface of the counterbore.

13. The system of claim 7, wherein an upper surface of the cap is substantially flush with the first surface of the plate when the elastic member is mounted to the plate.

14. The system of claim 7, wherein the counterbore is narrower than the elastic member in a neutral state with the elastic member in a pre-load condition in the first shape.

15. A screw retaining system comprising:
a plate with a first surface and a second surface;
an aperture that extends through the plate;
a counterbore that extends into the first surface, the counterbore extending a limited distance into the first surface and abutting with the aperture;
a resilient ring positioned in the counterbore and having a central section;
a cap having a flange and an outwardly-extending plug, the flange extending over the counterbore and having a curved edge that conforms to an outer circumference of the aperture such that the cap does not overlap with the aperture, the plug extending through the central section of the ring and into the plate; a section of the ring extending outward beyond the curved edge and into the aperture when the ring is in a first shape, and the section being at least partially positioned under the flange when the ring is in a second shape.

16. The system of claim 15, wherein the ring has a C-shape with first and second spaced apart ends that form a slot.

17. The system of claim 16, wherein the cap includes a tab that extends into the slot to limit rotation of the elastic member within the counterbore.

18. The system of claim 15, wherein the counterbore further comprises a receptacle that extends into the plate, the receptacle extending a greater depth into the plate from the first surface than the counterbore, the receptacle sized to receive the plug.

19. The system of claim 18, wherein the receptacle extends through the plate.

20. The system of claim 15, further comprising a second aperture that extends through the plate and abuts against the counterbore, the ring extending into the second aperture when the ring is in the first shape, and the flange including an outer edge that aligns with the second aperture such that the cap does not extend into the second aperture.

* * * * *